(12) United States Patent
Chanduszko et al.

(10) Patent No.: US 10,342,654 B2
(45) Date of Patent: *Jul. 9, 2019

(54) IVC FILTER WITH TRANSLATING HOOKS

(71) Applicant: C.R. Bard, Inc., Tempe, AZ (US)

(72) Inventors: Andrzej J. Chanduszko, Chandler, AZ (US); Scott L. Randall, Mesa, AZ (US); William R. Bratt, Tempe, AZ (US)

(73) Assignee: C.R. BARD, INC., Murray Hill, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/831,273

(22) Filed: Dec. 4, 2017

(65) Prior Publication Data

US 2018/0153673 A1 Jun. 7, 2018

Related U.S. Application Data

(60) Continuation of application No. 15/289,859, filed on Oct. 10, 2016, now Pat. No. 9,833,307, which is a
(Continued)

(51) Int. Cl.
*A61F 2/01* (2006.01)

(52) U.S. Cl.
CPC .......... *A61F 2/01* (2013.01); *A61F 2002/016* (2013.01); *A61F 2002/018* (2013.01);
(Continued)

(58) Field of Classification Search
CPC .... A61F 2/01; A61F 2/013; A61F 2/07; A61F 2/90; A61F 2/848; A61F 2/88; A61F 2/82; A61F 2/93; A61F 2002/016; A61F 2002/018; A61F 2210/0004; A61F 2210/0014; A61F 2220/0016; A61F 2230/0008; A61F 2230/005; A61F 2230/008; A61F 2250/0067; A61F 2310/00017; A61F 2310/00107; A61F 2310/00113; A61F 2310/00143; A61F 2310/00149; A61F 2310/00155; A61B 17/221; A61B 17/12122
(Continued)

(56) References Cited

U.S. PATENT DOCUMENTS 7,331,992 B2 * 2/2008 Randall .................... A61F 2/07
623/1.16

* cited by examiner

*Primary Examiner* — Manuel A Mendez
(74) *Attorney, Agent, or Firm* — Garvey, Smith & Nehrbass, Patent Attorneys, L.L.C.; Seth M. Nehrbass; Charles C. Garvey, Jr.

(57) ABSTRACT

A filter with translating hooks is described. The filter can include strut members having first and second struts connected by a connecting portion. A translating hook is disposed adjacent the connecting portion of the strut members, the hook including a first elongate member attached at one end to the first strut and a second elongate member attached at one end to a second strut, the opposite ends of the elongate members connected together to define a tip. The translating hooks are configured to bend toward a central axis of the filter when the filter is in a collapsed configuration for delivery to a blood vessel and recovery from a blood vessel, and away from the central axis of the filter when the filter is in an expanded configuration within a blood vessel such that the hooks engage a vessel wall.

20 Claims, 3 Drawing Sheets

Related U.S. Application Data division of application No. 14/961,783, filed on Dec. 7, 2015, now Pat. No. 9,486,305, which is a division of application No. 13/584,586, filed on Aug. 13, 2012, now Pat. No. 9,204,956, which is a continuation-in-part of application No. 12/299,300, filed as application No. PCT/US2007/009215 on Apr. 16, 2007, now Pat. No. 8,333,785, application No. 13/584,586, which is a continuation-in-part of application No. 13/009,727, filed on Jan. 19, 2011, now Pat. No. 8,241,350, which is a continuation of application No. 11/966,203, filed on Dec. 28, 2007, now Pat. No. 7,887,580, which is a continuation of application No. 10/079,155, filed on Feb. 20, 2002, now Pat. No. 7,331,992.

(60) Provisional application No. 60/797,006, filed on May 2, 2006.

(52) U.S. Cl.
CPC .......... *A61F 2210/0004* (2013.01); *A61F 2210/0014* (2013.01); *A61F 2220/0016* (2013.01); *A61F 2230/005* (2013.01); *A61F 2230/008* (2013.01); *A61F 2230/0008* (2013.01); *A61F 2250/0067* (2013.01); *A61F 2310/00017* (2013.01); *A61F 2310/00107* (2013.01); *A61F 2310/00113* (2013.01); *A61F 2310/00143* (2013.01); *A61F 2310/00149* (2013.01); *A61F 2310/00155* (2013.01)

(58) Field of Classification Search
USPC ........................................................ 606/200
See application file for complete search history.

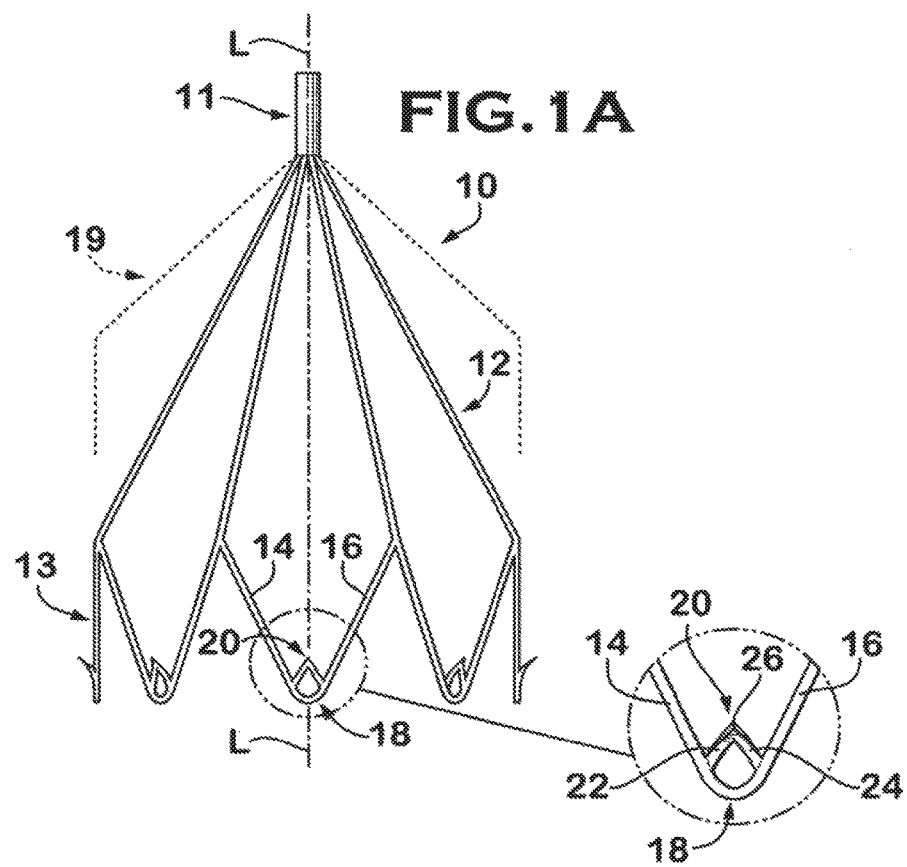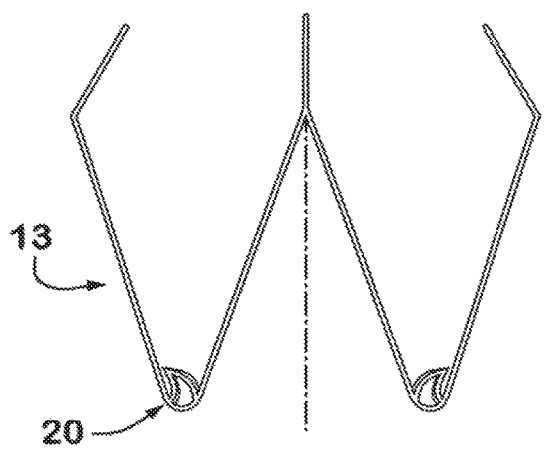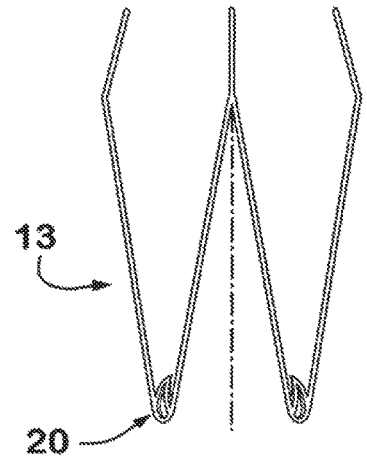

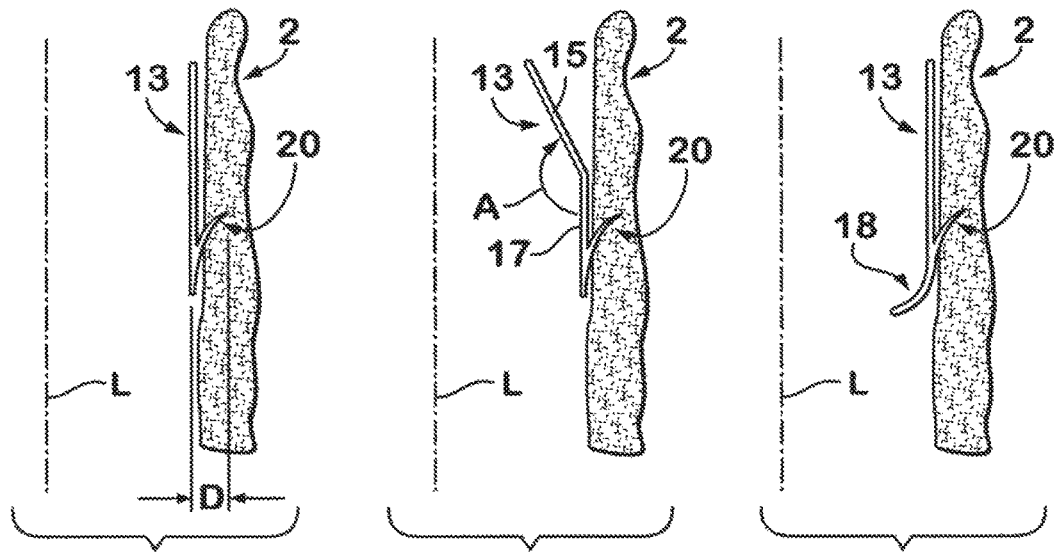
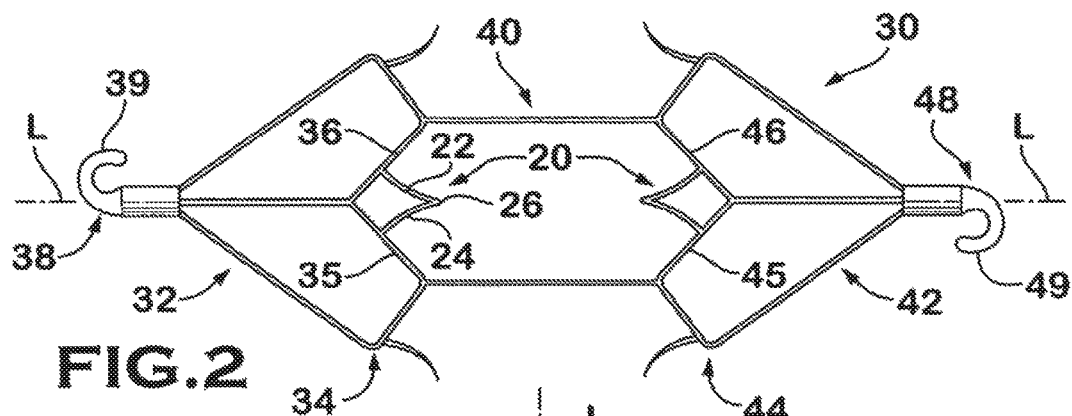
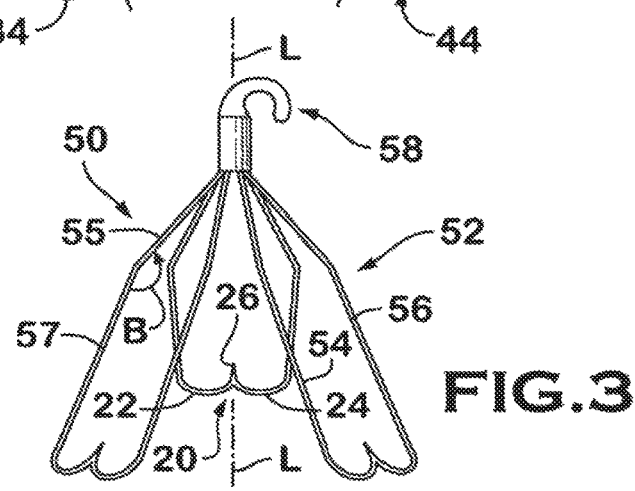

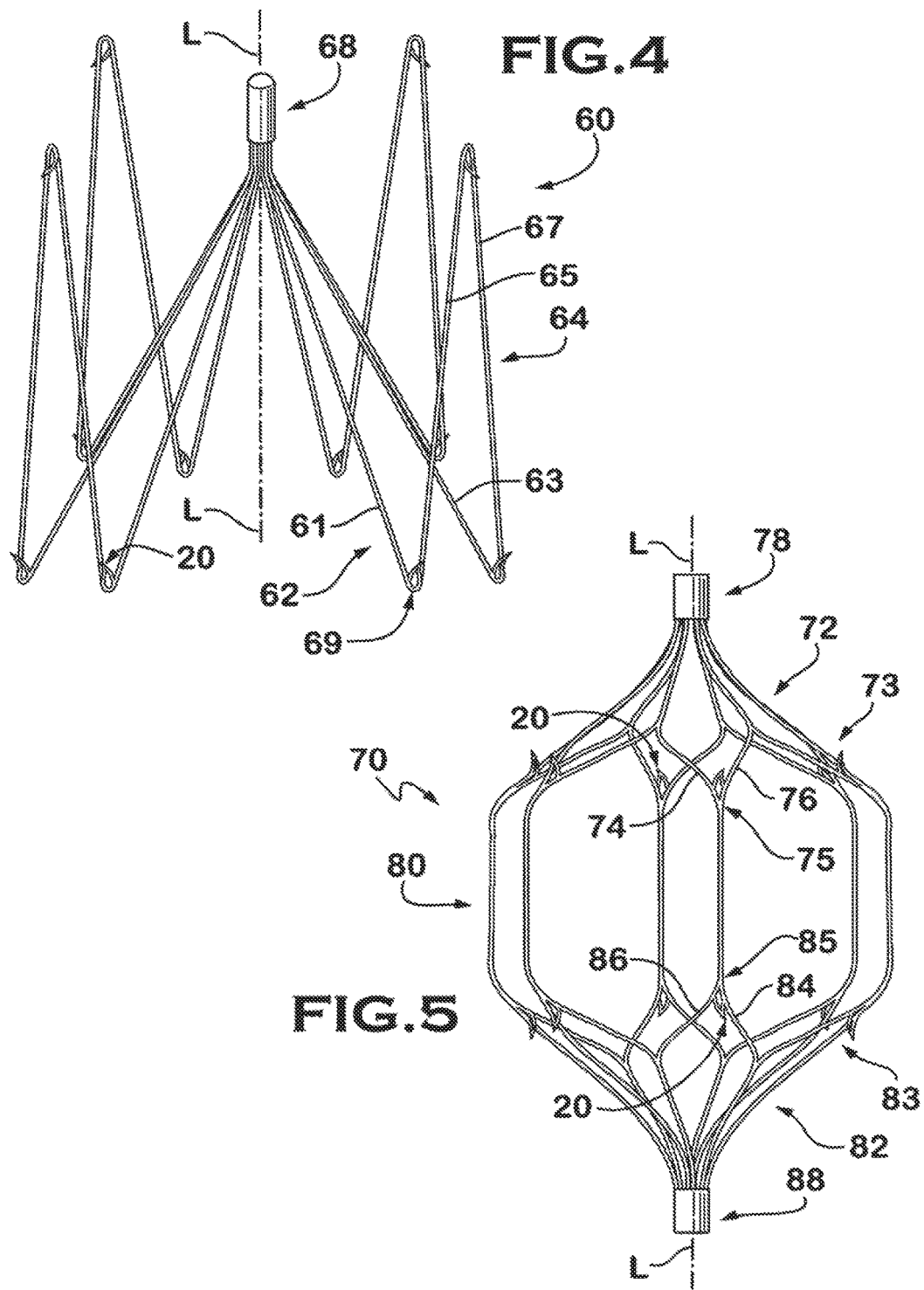

IVC FILTER WITH TRANSLATING HOOKS

PRIORITY

This application is a continuation of U.S. patent application Ser. No. 15/289,859, filed Oct. 10, 2016, now U.S. Pat. No. 9,833,307, which is a division of U.S. patent application Ser. No. 14/961,783, filed Dec. 7, 2015, now U.S. Pat. No. 9,486,305, which is a division of U.S. patent application Ser. No. 13/584,586, filed Aug. 13, 2012, now U.S. Pat. No. 9,204,956, which is a continuation-in-part of U.S. patent application Ser. No. 12/299,300, filed Feb. 24, 2009 as a U.S. national stage application under 35 U.S.C. § 371 of International Application No. PCT/US2007/009215, claiming the benefit of priority to U.S. Provisional Application No. 60/797,006, filed May 2, 2006; and which is a continuation-in-part of U.S. patent application Ser. No. 13/009,727, filed Jan. 19, 2011, now U.S. Pat. No. 8,241,350, which is a continuation of U.S. patent application Ser. No. 11/966,203, filed Dec. 28, 2007, now U.S. Pat. No. 7,887,580, which is a continuation of U.S. patent application Ser. No. 10/079,155, filed Feb. 20, 2002, now U.S. Pat. No. 7,331,992. Each of the aforementioned applications is incorporated by reference into this application as if fully set forth herein.

BACKGROUND

Inferior vena cava (IVC) filters are devices configured for insertion into the inferior vena cava to capture particles that may be present in the blood stream which, if transported to, for example, the lungs could result in serious complications and even death. Typically, IVC filters are utilized in patients who have a contraindication to anticoagulation or in patients developing clinically apparent deep vein thrombosis (DVT) and/or pulmonary embolism (PE). Patients who have recently suffered from trauma, have experienced a heart attack (myocardial infarction), or who have undergone major surgical procedure (e.g., surgical repair of a fractured hip, etc.) may develop clinically apparent DVT. When a thrombus clot loosens from the site of formation and travels to the lung, it may cause PE, a life-threatening condition. An IVC filter may be placed in the circulatory system to intercept one or more clots and prevent them from entering the lungs. IVC filters are either permanent or retrievable.

There are many different configurations for IVC filters, including those that include a central hub from which extend a plurality of struts that form filter baskets having a conical configuration, such as disclosed in U.S. Pat. No. 6,258,026, which is incorporated by reference in its entirety into this application. Other IVC filter configurations utilize wires and/or frame members to form straining devices that permit flow of blood while trapping larger particles. IVC filters are generally configured for compression into a small size to facilitate delivery into the inferior vena cava and subsequent expansion into contact with the inner wall thereof. The IVC filter may later be retrieved from the deployed site by compressing the legs, frame members, etc., depending on the filter configuration. Typically, an IVC filter will include hooks or anchoring members for anchoring the filter in position within the inferior vena cava. The hooks may be more elastic than the legs or frame members to permit the hooks to straighten in response to withdrawal forces, which facilitate withdrawal from the endothelium layer of the blood vessel without risk of significant injury to the vessel wall.

One type of hook or anchoring device for an endoprosthesis is shown in U.S. Pat. No. 5,843,167, in the form of an assembly that is attached to a graft. The assembly includes anchors which are attached to a graft on either end and which are connected by wire struts that extend along the length of the graft. These anchors have hooks that are formed on the end of short segments of wire that are secured to the anchor. The hooks are adapted to protrude radially outwardly upon deployment of the end prosthesis, extending a short distance beyond the bends of the anchor. U.S. Pat. No. 5,843,164 discloses an anchoring system that includes hooks to penetrate a vessel wall. The hooks are generally provided at each end of a stent graft, each hook having one or more barbs thereon. U.S. Pat. No. 5,591,197 discloses a different type of anchor in the form of deformable connecting members that attach cylindrical elements which together form a stent. Upon balloon expansion of the connecting members, a notched, weakened area is forced outward to form a barb to penetrate a vessel wall. U.S. Pat. No. 5,593,434 discloses a plurality of projections or teeth cut away from a sheet of material, which is curled into a cylinder to form a stent. One possible drawback to these and other anchoring systems is that the teeth or hooks attached or integrated into the grafts or stents have a tendency to catch on the delivery sheaths or catheters during deployment. This creates problematic situations in the deployment process as the teeth or hooks tear the sheath material, preventing the necessary precision required in percutaneous delivery into a body lumen.

The following references relate to filters: U.S. Pat. Nos. 5,324,304; 6,972,025; U.S. Patent Application Publication No. 2003/0176888; U.S. Patent Application Publication No. 2004/0193209; U.S. Patent Application Publication No. 2005/0267512; and U.S. Patent Application Publication No. 2005/0267515, each of which is incorporated by reference in its entirety into this application.

Applicants have recognized that it would be desirable to provide an IVC filter that incorporates translating hooks, such that delivery to and from a body vessel is facilitated. Embodiments of such IVC filters are described herein.

SUMMARY

Accordingly, described herein is a filter incorporating translating hooks. In one embodiment, a filter includes a body including a plurality of strut members disposed about a central axis to define an outer perimeter, each of the strut members including a first strut and a second strut, the body having a first outer perimeter in a first configuration and a second outer perimeter larger than the first outer perimeter in a second configuration, and a hook disposed between the first and second struts of at least one of the strut members, the hook having a first elongate member connected to a second elongate member to define a tip, the first elongate member having an end portion coupled to the first strut and the second elongate member having an end portion coupled to the second strut so that in the first configuration, the tip is oriented toward the central axis in a first direction, and in the second configuration, the tip is oriented away from the central axis in a second direction.

In another embodiment, a filter includes a body having a plurality of struts, each strut having a proximal end connected to a head and a distal end, with adjacent struts connected at their distal end by a connecting portion such that the body includes a plurality of distal connecting portions, and at least one of the plurality of distal connecting portions including a hook having an apex formed by the joining of a first elongate member and a second elongate member, the first elongate member attached to a first of said adjacent struts and the second elongate member attached to a second of said adjacent struts.

In one embodiment, a method of anchoring and recovering a filter in a blood vessel includes introducing the filter into a blood vessel, the filter comprising at least one hook including first and second portions that are joined together at one end thereof to form a tip and that are attached respectively to different portions of a filter body at an opposite end thereof, and expanding the first and second portions to direct the tip of the hook away from a central axis defined by the filter body such that the tip of the hook engages a wall of the blood vessel.

These and other embodiments, features and advantages will become more apparent to those skilled in the art when taken with reference to the following more detailed description of the invention in conjunction with the accompanying drawings that are first briefly described.

BRIEF DESCRIPTION OF THE DRAWINGS

FIG. 1A is front perspective view of one embodiment of a filter with translating hooks in an expanded configuration and an enlarged view of a translating hook.

FIGS. 1B-1C are illustrations of a strut member of the filter of FIG. 1A, shown respectively in an expanded and collapsed position.

FIG. 1D is a side view of an embodiment of a strut member for a filter, shown with a hook embedded in a blood vessel wall.

FIG. 1E is a side view of another embodiment of a strut member for a filter, shown with a hook embedded in a blood vessel wall.

FIG. 1F is a side view of yet another embodiment of a strut member for a filter, shown with a hook embedded in a blood vessel wall.

FIG. 2 is a side perspective view of a symmetrical filter with translating hooks, including dual retrieval members.

FIG. 3 is a front perspective view of one embodiment of a filter with translating hooks, including a retrieval member.

FIG. 4 is a perspective view of another embodiment of a filter with translating hooks.

FIG. 5 is a side perspective view of another embodiment of a filter with translating hooks.

DETAILED

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

While the examples provided herein are discussed with respect to IVC filters, it should be appreciated that the filter embodiments described herein could be used for filter applications that do not involve placing a filter device in the inferior vena cava. In other words, the filters described herein are not limited to IVC applications.

Further, as used herein the term "bio-resorbable" includes a suitable biocompatible material, mixture of various biocompatible materials or partial components of biocompatible material being altered into other materials by an agent present in the environment (e.g., a biodegradable material that degrades via a suitable mechanism such as hydrolysis when placed in biological tissue); such materials being removed by cellular activity or incorporated into the cellular structure (i.e., bioresorption, bioresorping, bioabsorption, or bioresorbable), such materials being degraded by bulk or surface degradation (i.e., bioerosion such as, for example, a water insoluble polymer that turns water-soluble in contact with biological tissue or fluid), or such materials being altered by a combination of one or more of biodegradable, bioerodable or bioresorbable activity when placed in contact with biological tissue or fluid.

Possible materials for the filters, or portions thereof, described herein include a suitable biocompatible material such as, for example, stainless steel, noble metals and their alloys, shape memory metals, shape memory alloys, super elastic metal, super elastic shape memory metal alloys, linear elastic shape memory metal, metal alloys, Phynox, Conichrome, titanium, stainless steel, shape memory polymers, polymers, bio-materials (e.g., metal alloys such as those shown and described in U.S. Pat. No. 6,287,332 and U.S. Patent Application Publication No. 2002/0004060, each of which is incorporated by reference in its entirety into this application), and combinations thereof. The filters, or portions thereof, described herein may include an anti-stick material on one or more surfaces. Examples of anti-stick materials, include, for example, fluorinated polytetrafluoroethylene (PTFE), polyurethane, and combinations thereof.

Where the filter is to be utilized with bio-active agents to control the formation of emboli, bio-active agents can be coated to a portion or the entirety of the filter for controlled release of the agents once the filter is implanted. The bio-active agents can include, but are not limited to, vasodilator, anti-coagulants, such as, for example, warfarin and heparin. Other bio-active agents can include, but are not limited to, agents such as, for example, anti-proliferative/ antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as G(GP) $II_b/III_a$ inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine (cladribine)); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetaminophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Referring now to FIG. 1A, a filter 10 is shown, including a hub 11, a set of legs 12 and a set of strut members 13. The filter 10 is illustrated in FIG. 1A in an expanded configuration, defining an expanded perimeter. The hub 11 may include a retrieval member (e.g., a hook-like member) to facilitate retrieval of the filter 10 from the blood vessel. Optionally, shown in phantom, the filter 10 may also include a set of arms 19, which in one embodiment are shorter in length than the legs 12. The arms in one embodiment have a proximal end joined at the hub 11, extending first outwardly with respect to the central axis L of the filter 10 when the filter is in the expanded configuration to a shoulder and then distally with respect to the hub 11 and angularly with respect to the shoulder. The arms 19 may provide a centering function to the filter 10 and may include hooks or vessel-engaging members on their distal ends. Each leg 12 has a proximal end joined at the hub 11, extending radially outward from a central axis L when the filter 10 is in an expanded or deployed configuration, while each strut member 13 is positioned generally parallel to the central axis L when the filter 10 is in an expanded configuration. In this embodiment, there are an even number of legs 12, preferably eight, although any number of legs is possible and within the scope of the invention. For delivery of the filter 10 to a blood vessel, the filter 10 is compressed to a collapsed configuration, defining a collapsed perimeter smaller than the expanded perimeter, the set of legs 12 and set of strut members 13 being positioned generally parallel to the central axis L when the filter is in the collapsed configuration.

Each of the strut members 13 include a first strut 14 and a second strut 16 that have a proximal end connected to a distal end of adjacent legs 12 (i.e., the proximal end of the first strut 14 is connected to a distal end of one leg 12 and the proximal end of the second strut 16 is connected to the distal end of an adjacent leg 12). The first strut 14 and second strut 16 are connected at a distal end thereof by a connecting portion 18, which in the embodiment shown in FIG. 1A is a rounded, semi-circular shape, but which in other embodiments can be various other shapes. The connecting portion 18 can be a separate piece of material attached to the first and second struts 14, 16, but in the preferred embodiment, the first strut 14, second strut 16 and connecting portion 18 are one continuous member, created through processes known to one skilled in the art (e.g., molding, laser cutting of a tube or a sheet, etching, electro-discharge-machining). A hook 20 is disposed between the first strut 14 and second strut 16, the hook 20 including a first elongate member 22, connected at a distal end to the first strut 14, and a second elongate member 24, connected at a distal end to the second strut 16, the first and second elongate members 22, 24 connected together at a proximal end thereof to define a tip or apex 26 as best seen in the enlarged view of FIG. 1A. Although a hook 20 is shown in FIG. 1A between each of the strut members 13, in other embodiments only select strut members 13 include a hook 20 (e.g., in a filter including eight strut members 13, only four strut members 13 include a hook with no two adjacent strut members 13 including hooks, etc.).

The hook 20 is configured such that the tip 26 is oriented away from the central axis L of the filter 10 in an expanded configuration (FIG. 1B), but oriented toward the central axis L of the filter 10 in a collapsed configuration (FIG. 1C), such that depending on the configuration of the filter 10, the tip 26 of the hook 20 can be oriented in different directions. The characteristic of the hook 20, in which the tip 26 is oriented in a different direction depending on the configuration of the filter, can be established, for example, through material properties of the hook 20, positioning of the hook 20 with respect to the first and second struts 14, 16, and/or shape of the elongate members 22, 24 (e.g., thickness, width, curvature, etc.) that form the hook 20. For instance, the angle formed between the first elongate member 22 and second elongate member 24, coupled with the stiffness of the material of the elongate members 22, 24 and the shape of thereof (e.g., slightly curved, tapered, decreasing thickness from the attachment end of the elongate members to the tip, etc.) can contribute to the directional orientation of the tip 26 in the expanded and collapsed configurations of the filter 10. Thus, the included angle defined by the tip between the expanded and collapsed configurations of the filter 10 can be equal to, greater than, or less than 180 degrees, although the presently preferred embodiment is less than 180 degrees. The change in orientation of the hook 20 depending on the configuration of the filter (i.e., expanded or collapsed) is described herein as "translation" of the hook, such that the filter 10 includes one or more "translating hooks." Examples of embodiments of a translating hook 20 can be found in U.S. Patent Application Publication No. 2003/0158595, which is incorporated by reference in its entirety into this application. The potential materials for the hook 20 are the same as those discussed herein as possible materials for the filter.

As shown in FIG. 1D, the orientation of the tip 26 of the hook 20 away from the central axis L when the filter 10 is in the expanded configuration results in the hook 20 becoming at least partially embedded into a blood vessel wall 2 when the filter 10 is deployed in the blood vessel. As shown, the depth penetration limit of the hook 20 is the distance D between the tip 26 and the distal end of the elongate members 24, 26 attached to the first and second struts 14, 16, respectively. FIG. 1F illustrates an embodiment for strut members 13 in which the connecting portion 18 is formed with a curvature that is oriented in a direction toward the central axis L. By orienting the connection portion 18 away from the blood vessel wall 2, tissue ingrowth into the strut members 13 is believed to be prevented, which facilitates removal of the filter 10 from the blood vessel. FIG. 1E illustrates an embodiment for strut members 13 in which an angle A is formed between a proximal section 15 and distal section 17 of the strut member 13 (i.e., a proximal and distal section of both of first and second struts 14, 16), such that the proximal section 15 of the strut member 13 is not in contact with the blood vessel wall 2, imparting a limited contact area (i.e., distal section 17) to the strut member 13. As a result, tissue ingrowth into the proximal section 15 is believed to be prevented, facilitating removal of the filter 10 from the blood vessel. In the example shown, the distal section 17 is generally parallel to the central axis L when the filter 10 is in the expanded configuration and the proximal section 15 is oriented in a direction toward the central axis L. The angle A between the proximal section 15 and distal section 17 of the strut member 13 is in the range of approximately 95 degrees to approximately 150 degrees, preferably in the range of approximately 110 degrees to approximately 130 degrees.

FIG. 2 illustrates a symmetrical retrievable filter 30, including a first hub 38 and a second hub 48, each hub containing a retrieval member 39, 49 with a hook-like configuration. The filter 30 is illustrated in an expanded configuration, defining an expanded perimeter. A first set of legs 32 extends from the first hub 38 radially outward from a central axis L, each leg 32 joined at a proximal end thereof to the first hub 38 and at a distal end to the first set of strut members 34. In the embodiment shown, each of the strut members 34 includes a first strut 35 and a second strut 36 that are proximally connected at the intersection of the leg 32 with the strut member 34. Thus, as shown, each leg 32 and strut member 34 together form a "Y" shape. The distal ends of the first and second struts 35, 36 are connected to adjacent struts 36, 35, respectively, of strut members 34 at the intersection of a connecting member 40, which lies approximately parallel to the central axis L and connects the first strut members 34 to the second strut members 44. Each of the second strut members 44 includes a first strut 45 and a second strut 46 that are proximally connected at the intersection of a leg 42 with the strut member 44 (also forming a "Y" shape with the leg 42). The distal ends of the first and second struts 45, 46 are connected to adjacent struts 46, 45, respectively, of strut members 44 at the intersection of the connecting member 40. A second set of legs 42 extends from the second hub 48 radially outward from a central axis L, each leg 42 joined at a proximal end thereof to the second hub 48 and at a distal end to the second set of strut members 44 as described.

Translating hooks 20 are attached to each of the strut members 34, 44 such that a first elongate member 22 is connected at a distal end to a first strut 35, 45 and a second elongate member 24 is connected to a second strut 36, 46, the elongate members 22, 24 connected together at a proximal end thereof to define a tip 26. The hooks 20 may be attached to each strut member 34, 44 or select strut members 34, 44. As shown in FIG. 2, the configuration of the filter 30 is such that the hooks 20 attached to the first strut members 34 are oriented toward the hooks 20 attached to the second strut members 44 and vice versa. This orientation facilitates withdrawal of the filter 30 from a blood vessel as it permits retrieval of the filter 30 from either a jugular or femoral approach by using a suitable recovery device, such as, for example, a cone type similar to the device shown and described in U.S. Pat. No. 6,156,055, which is incorporated by reference in its entirety into this application. The translating hook 20 is configured such that the tip 26 is oriented away from the central axis L of the filter 30 in an expanded configuration, but oriented toward the central axis L of the filter 30 in a collapsed configuration, such that depending on the configuration of the filter 30, the tip 26 of the hook 20 can be oriented in different directions, as discussed above.

Filter 30 in one embodiment is cut from a tube of material, such as Nitinol. The particulars of cutting a filter from a tube of material, along with exemplary embodiments of such is shown and described in International Patent Application No. PCT/US2007/06003, filed Mar. 8, 2007, claiming priority to U.S. Provisional Patent Application No. 60/782,019, filed Mar. 14, 2006, each of which is incorporated by reference in its entirety into this application.

Referring now to FIG. 3, a filter 50 includes a set of strut members 52, each of the strut members including a first strut 54 and a second strut 56. The first and second struts 54, 56 are joined at a proximal end to a hub 58, which can include a retrieval member as shown. The strut members 52 can be arranged, such as shown in FIG. 3, to overlap one another such that the outer surface of one strut member 52 is adjacent an inner surface of an adjacent strut member 52. The distal ends of the first and second struts are connected to a translating hook 20, including a first elongate member 22 and a second elongate member 24. The first strut 54 is connected to the distal end of the first elongate member 22 and the second strut 56 is connected to the distal end of the second elongate member 24, the elongate members 22, 24 connected together at a proximal end thereof to define a tip 26. Thus, in this embodiment, the hook 20 connects the first strut 54 to the second strut 56. The elongate members 22, 24 have a curved configuration in the embodiment shown in FIG. 3, together with the struts 54, 56 forming a lobed configuration. The translating hook 20 is configured such that the tip 26 is oriented away from the central axis L of the filter 50 in an expanded configuration, but oriented toward the central axis L of the filter 50 in a collapsed configuration, such that depending on the configuration of the filter 50, the tip 26 of the hook 20 can be oriented in different directions, as discussed above.

The first strut 54 and second strut 56 can include a proximal section 55 and a distal section 57 that are angled with respect to one another such that an angle B is formed therebetween. Proximal section 55 extends from the hub 58, while distal section 57 is connected to the hook 20. Angle B can be different for the first and second struts 54, 56, or angle B can be the same for the first and second struts 54, 56 in one strut member 52, but different for the first and second struts 54, 56 in an adjacent strut member. The angle B between the proximal section 55 and distal section 57 is in the range of approximately 95 degrees to approximately 170 degrees, preferably in the range of approximately 120 degrees to approximately 150 degrees.

FIG. 4 illustrates a filter 60, including four appendages 62 connected proximally to a hub 68. Although not shown in FIG. 4, the hub 68 can include a retrieval member. Also, although four appendages 62 are shown in this embodiment, the filter 60 could instead have two, three, five, six, etc. appendages. The appendages 62 include a first leg 61 and a second leg 63, each of which have a proximal end joined at the hub 68, and extend radially outward from a central axis L when the filter 60 is in an expanded configuration (as shown). Connected to the distal ends of each of the legs 61, 63 is a strut member 64, including a first strut 65 and a second strut 67. The proximal end of the first strut 65 is connected via a connecting portion 69 to the first leg 61, while the proximal end of the second strut 67 is connected via a connecting portion 69 to the second leg 63. The distal ends of the first strut 65 and the second strut 67 are also connected together via a connecting portion 69. The connecting portions 69 can be separate members attached to the legs and struts and can be of different shapes and sizes; however, in the preferred embodiment, the legs, struts and connecting portions are one continuous member, created through processes known to one skilled in the art (e.g., molding, laser cutting of a tube or a sheet, etc.). Thus, each appendage 62 includes three connecting portions 69, which as shown in FIG. 4, are adjacent the outer perimeter of the filter 60 in the expanded configuration.

Disposed adjacent each of the connecting portions 69 are translating hooks 20, including elongate members 22, 24 connected together at a proximal end thereof to define a tip 26. The distal ends of the elongate members 22, 24 are attached respectively to first and second struts 65, 67, to first leg 61 and first strut 65 and to second leg 63 and second strut 67 as shown. In other embodiments, translating hooks 20 are disposed only between first and second struts 65, 67 of each appendage 62, or select appendages 62. In still other embodiments, translating hooks 20 are disposed only between legs and struts of each appendage 62 or select appendages. The translating hooks 20 are configured such that the tips 26 are oriented away from the central axis L of the filter 60 in an expanded configuration, but are oriented toward the central axis L of the filter 60 in a collapsed configuration, such that depending on the configuration of the filter 60, the tips 26 of the hooks 20 can be oriented in different directions, as discussed above. In addition to the translating hooks 20, one or more vessel engaging members may be positioned along the length of the appendages 62.

FIG. 5 illustrates a filter 70, including a first hub 78 and a second hub 88. Although not shown, in some embodiments, one or both of the hubs 78, 88 may include a retrieval member. Extending from the first hub 78 is a first set of legs 72 connected to a first set of strut members 73, the strut members 73 including a first strut 74 and a second strut 76 that each have an end connected to an end of adjacent legs 72 (i.e., the end of the first strut 74 of a strut member 73 is connected to an end of one leg 72 and the end of the second strut 76 of a strut member 73 is connected to an end of an adjacent leg 72). The end of a first strut 74 of one strut member 73 is connected to the same leg 72 as that of a second strut 76 of an adjacent strut member 73, as shown, such that a plurality of connected cells are formed. The opposite ends of the first and second struts 74, 76 of a strut member 73 are connected together to form the shape of a spade when the filter 70 is in an expanded configuration (as shown) with an end 75 that is connected to a connecting member 80. Disposed adjacent the tips 75 are translating hooks 20, including elongate members 22, 24 connected together at a proximal end thereof to define a tip 26. The translating hooks 20 are configured such that the tips 26 are oriented away from the central axis L of the filter 70 in an expanded configuration (as shown), but are oriented toward the central axis L of the filter 70 in a collapsed configuration, such that depending on the configuration of the filter 70, the tips 26 of the hooks 20 can be oriented in different directions, as discussed above.

Extending from the second hub 88 is a second set of legs 82 connected to a second set of strut members 83, the strut members 83 including a first strut 84 and a second strut 86 that each have an end connected to an end of adjacent legs 82 (i.e., the end of the first strut 84 of a strut member 83 is connected to an end of one leg 82 and the end of the second strut 86 of a strut member 83 is connected to an end of an adjacent leg 82). The end of a first strut 84 of one strut member 83 is connected to the same leg 82 as that of a second strut 86 of an adjacent strut member 83, as shown, such that a plurality of connected cells are formed. The opposite ends of the first and second struts 84, 86 of a strut member 83 are connected together to form the shape of a spade when the filter 70 is in an expanded configuration (as shown) with an end 85 that is connected to a connecting member 80. Disposed adjacent the tips 85 are translating hooks 20, including elongate members 22, 24 connected together at a proximal end thereof to define a tip 26, the tips 26 of the hooks 20 configured to be oriented in different directions depending on the configuration of the filter 70, as discussed above. The connecting members 80 connect the tips 75 to the tips 85 and are lie generally parallel to the longitudinal axis in both the expanded and collapsed configurations of filter 70. Details of the filters shown in FIGS. 4 and 5 are further shown and described in U.S. Pat. Nos. 6,517,573 and 6,443,972, each of which is incorporated by reference in its entirety into this application.

One particular advantage recognized by applicants of incorporating one or more translating hooks into a filter is that during delivery of the filter to a blood vessel or other bodily cavity, the tips of the hooks are oriented toward the central axis of the filter such that the risk of engaging the hooks with the introducer catheter is greatly minimized. More particularly, because the tips of the hooks are retracted completely away from a sheath or delivery catheter used to introduce the filter into a body lumen, any relative movement of the sheath and the filter will not result in undesirable events, such as tearing of the sheath or catching of the filter on the sheath, which could potentially lead to misalignment of the filter in the vessel, release of sheath material into the body, or other potentially dangerous outcomes. In one particular embodiment, the filter is collapsed for inserting in a delivery catheter having an inside surface defining an inside diameter (ID) of less than 9 French, such that the translating hooks are spaced apart from the inside surface of the catheter. In the same way, recovery of a filter with translating hooks avoids the aforementioned undesirable events; when the filter is compressed to a collapsed configuration from an expanded deployed configuration of the filter in a vessel, the translating hooks bend toward the central axis of the filter for safe retraction from the vessel.

The use of a shape memory material, such as Nitinol, for the arms, legs, or hooks facilitates collapsing the filter radially inward from its normally expanded (i.e., unconstrained) configuration toward its longitudinal axis into a collapsed configuration for insertion into a body vessel. The properties of Nitinol allow the filter members to withstand enormous deformations (e.g., eight times as much as stainless steel) without having any effect of the filter ability to recover to the pre-determined shape. This is due to the crystal phase transitions between rigid austenite and softer martensite, which phenomenon enables the implant to be loaded into a very small diameter sheath for delivery, significantly reducing the potential trauma and complications to the insertion site. Transition between the martensitic and austenitic forms of the shape memory material can be achieved by increasing or decreasing the material deformation above and below the transition stress level while the material remains above the transition temperature range, specifically Af. This is particularly important in the case of the hooks, as they may be deformed significantly (hence, becoming martensitic) while the filter is challenged by clots. The super-elastic properties will allow the hooks to re-assume their intended shape as soon as the load is released (e.g. the clot breaks down).

The hooks may be retrieved from the Inferior Vena Cava ("IVC") wall during the filter removal when longitudinal force is applied to the hub in the direction of the blood flow. Under this concentrated stress, the hooks will deform and transition to the martensitic state, thereby becoming super-elastic. Thus, the hooks are designed to bend when a specific retrieval force is applied and spring back to their original shape once the retrieval force is removed. Alternatively, a reduction in temperature below the Af temperature can be applied to the shape memory material to cause a change in the crystalline phase of the material, thereby rendering the material malleable during loading or retrieval of the filter. Various techniques can be used to cause a change in crystalline phase such as, for example, cold saline, low temperature fluid or thermal conductor.

By virtue of the characteristics of thermal shape memory material, the filter members can be cooled below the martensitic-to-austenitic transition temperature, and then straightened and held in a collapsed, straight form that can pass through a length of fine plastic tubing with an internal diameter of approximately 2 millimeters (mm), e.g., a #8 French catheter. In its high temperature form (as in a mammalian body), the filter recovers to a preformed filtering shape. Alternatively, the legs or arms may be made of wires of spring metal which can be straightened and compressed within a catheter or tube and will diverge into a deployed shape when the tube is removed.

The deployed shapes and configurations of the filter members can be set (imprinted with a memory shape) by annealing the members at high temperature (e.g. 500° C.) while holding them in the desired shape. Thereafter, whenever the filter is in the austenitic form (i.e., at a temperature above the martensitic-to-austenitic transition temperature or Af temperature), the members return to the memory shape. Example methods for setting the high-temperature shape of filters are disclosed in U.S. Pat. No. 4,425,908, which is incorporated by reference in its entirety into this application.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A filter hook system comprising:
   a) a plurality of legs, each leg having proximal and distal leg end portions;
   b) first and second struts, each strut having proximal and distal strut end portions, each strut connected to a said leg distal end portion at a proximal strut end portion;
   c) each strut having a distal end portion connected to another strut distal end portion by a connecting portion;
   d) said legs including first and second elongate j g members connected to each other at the proximal leg end portions and each leg connected at the distal leg end portions to the first and second struts; and
   e) said first and second struts supporting one or more anchors at a position distally of the legs.

2. The filter hook system of claim 1 wherein in a first position the proximal leg ends protrude from a plane's first side and in a second position the proximal leg ends protrude from the plane's opposite side.

3. The filter hook system of claim 2 wherein the first and second struts have been adapted to connect to a hub.

4. The filter hook system of claim 3 wherein the connecting portion has been adapted to connect to a bridge connected to a different connecting portion.

5. A filter hook system comprising:
   first and second struts connected by a connecting portion;
   first and second elongate members connected to each other at first ends to form a tip and connected at second ends to the first and second struts; and
   wherein the first and second struts define a variable included angle with a vertex on the connecting portion wherein smaller angles yield the tip situated in a plane of the struts and angle variation to larger included angles yields the tip protruding from the plane.

6. The filter hook system of claim 5 wherein the tip and the elongate members are biased.

7. The filter hook system of claim 6 wherein the tip, the elongate members, and the struts are a biased assembly.

8. The filter hook system of claim 7 wherein, the plane has a first side and an opposite side, and wherein in a first position the tip protrudes from the plane's first side and in a second position the tip protrudes from the plane's opposite side.

9. The filter hook system of claim 8 wherein the first and second struts have been adapted to connect to a hub.

10. The filter hook system of claim 9 wherein the hub comprises spacer wires.

11. The filter hook system of claim 10 wherein the connecting portion has been adapted to connect to a bridge connected to a different connecting portion.

12. The filter hook system of claim 11 that has been adapted for a vascular filter.

13. The filter hook system of claim 12 that has been adapted for a retrievable vascular filter.

14. The filter hook system of claim 13 wherein the hub comprises a retrieval member.

15. The filter hook system of claim 9 wherein the hub comprises spacer wires.

16. The filter hook system of claim 15 wherein the first and second struts have been adapted for a vascular filter.

17. The filter hook system of claim 16 wherein the first and second struts have been adapted for a retrievable vascular filter.

18. The filter hook system of claim 9 that has been adapted for a vascular filter.

19. The filter hook system of claim 18 that has been adapted for a retrievable vascular filter.

20. A filter hook system comprising a biased assembly comprising:
   first and second struts connected by a connecting portion;
   first and second elongate members connected to each other at first ends to form a tip and connected at second ends to the first and second struts;
   wherein
   the first and second struts define a variable included angle with a vertex on the connecting portion wherein smaller angles yield the tip situated in a plane of the struts, the plane having a first side and an opposite side, and angle variation to larger included angles yields the tip protruding from the plane, in a first position the tip protrudes from the plane's first side in a second position the tip protrudes from the plane's opposite side, the first and second struts have been adapted to connect to a hub comprising a retrieval member and spacer wires, and the system has been adapted for a retrievable vascular filter.

* * * * *

UNITED STATES PATENT AND TRADEMARK OFFICE
CERTIFICATE OF CORRECTION

PATENT NO. : 10,342,654 B2
APPLICATION NO. : 15/831273
DATED : July 9, 2019
INVENTOR(S) : Andrzej J. Chanduszko, Scott L. Randall and William R. Bratt It is certified that error appears in the above-identified patent and that said Letters Patent is hereby corrected as shown below:

In the Claims

Column 11, Line 64, "j g" should be replaced with "leg".

Column 12, Line 1, "c)" should be replaced with "e)".

Signed and Sealed this
Thirteenth Day of August, 2019

Andrei Iancu
*Director of the United States Patent and Trademark Office*